(12) United States Patent
Crucs et al.

(10) Patent No.: US 7,896,229 B2
(45) Date of Patent: Mar. 1, 2011

(54) AUTO-DISTRIBUTION OF SCANNED DIGITAL IMAGES BASED ON STANDARDIZED IDENTIFIERS

(75) Inventors: Kevin M. Crucs, Akron, OH (US); Patrick James Williams, Cuyahoga Falls, OH (US)

(73) Assignee: Apteryx, Inc., Akron, OH (US)

( * ) Notice: Subject to any disclaimer, the term of this patent is extended or adjusted under 35 U.S.C. 154(b) by 476 days.

(21) Appl. No.: 12/035,913

(22) Filed: Feb. 22, 2008

(65) Prior Publication Data
US 2009/0212107 A1  Aug. 27, 2009

(51) Int. Cl.
G06F 17/00 (2006.01)
(52) U.S. Cl. ...................................... 235/375
(58) Field of Classification Search .................. 235/375
See application file for complete search history.

(56) References Cited

U.S. PATENT DOCUMENTS

| | | | |
|---|---|---|---|
| 4,498,005 A | | 2/1985 | Oono et al. |
| 5,072,119 A | | 12/1991 | Yamaguchi |
| 5,195,123 A | * | 3/1993 | Clement ..................... 378/166 |
| 5,264,684 A | | 11/1993 | Weil |
| 5,334,851 A | | 8/1994 | Good et al. |
| 5,376,806 A | | 12/1994 | Hejazi |
| 5,416,823 A | * | 5/1995 | Livingston .................. 378/166 |
| 5,418,355 A | | 5/1995 | Weil |
| 5,592,374 A | | 1/1997 | Fellegara et al. |
| 6,249,596 B1 | | 6/2001 | Buytaert et al. |
| 6,356,652 B1 | | 3/2002 | Vuylsteke |
| 6,864,917 B2 | | 3/2005 | Malloy Desormeaux |
| 7,182,021 B2 | | 2/2007 | Maehashi |
| 7,289,132 B1 | | 10/2007 | Reid et al. |
| 7,448,533 B2 | | 11/2008 | Ito |
| 2001/0009454 A1 | | 7/2001 | Manico et al. |
| 2002/0129488 A1 | | 9/2002 | Lieberman |
| 2004/0169149 A1 | | 9/2004 | Alzner et al. |
| 2005/0036692 A1 | | 2/2005 | Iida et al. |
| 2005/0098619 A1 | | 5/2005 | Ito et al. |
| 2005/0117031 A1 | | 6/2005 | Russon et al. |
| 2005/0195214 A1 | | 9/2005 | Reid et al. |
| 2006/0064639 A1 | | 3/2006 | Reid et al. |
| 2006/0066453 A1 | | 3/2006 | Homanfar et al. |
| 2006/0138211 A1 | * | 6/2006 | Lubow ....................... 235/375 |
| 2007/0018125 A1 | | 1/2007 | Fletcher-Heath et al. |

FOREIGN PATENT DOCUMENTS

| JP | 60-62404 A | 3/1994 |
|---|---|---|
| JP | 2003-091050 A | 3/2003 |

OTHER PUBLICATIONS

PCT/US2009/033743 International Search Report and Written Opinion.

* cited by examiner

*Primary Examiner*—Jamara A Franklin
(74) *Attorney, Agent, or Firm*—Hahn Loeser & Parks LLP

(57) ABSTRACT

A system and methods for facilitating the automatic distribution of acquired images within a medical facility. Apparatus capable of displaying digital images within two or more operatories is provided. Apparatus capable of scanning scannable image media is also provided, to read an encoded identifier and a captured image from each of the scannable image media. The encoded identifier of any given scannable image medium is associated with one operatory of the medical facility. Apparatus capable of transmitting a read image to the apparatus capable of displaying digital images within a particular operatory in dependence on the read associated identifier is further provided.

25 Claims, 10 Drawing Sheets

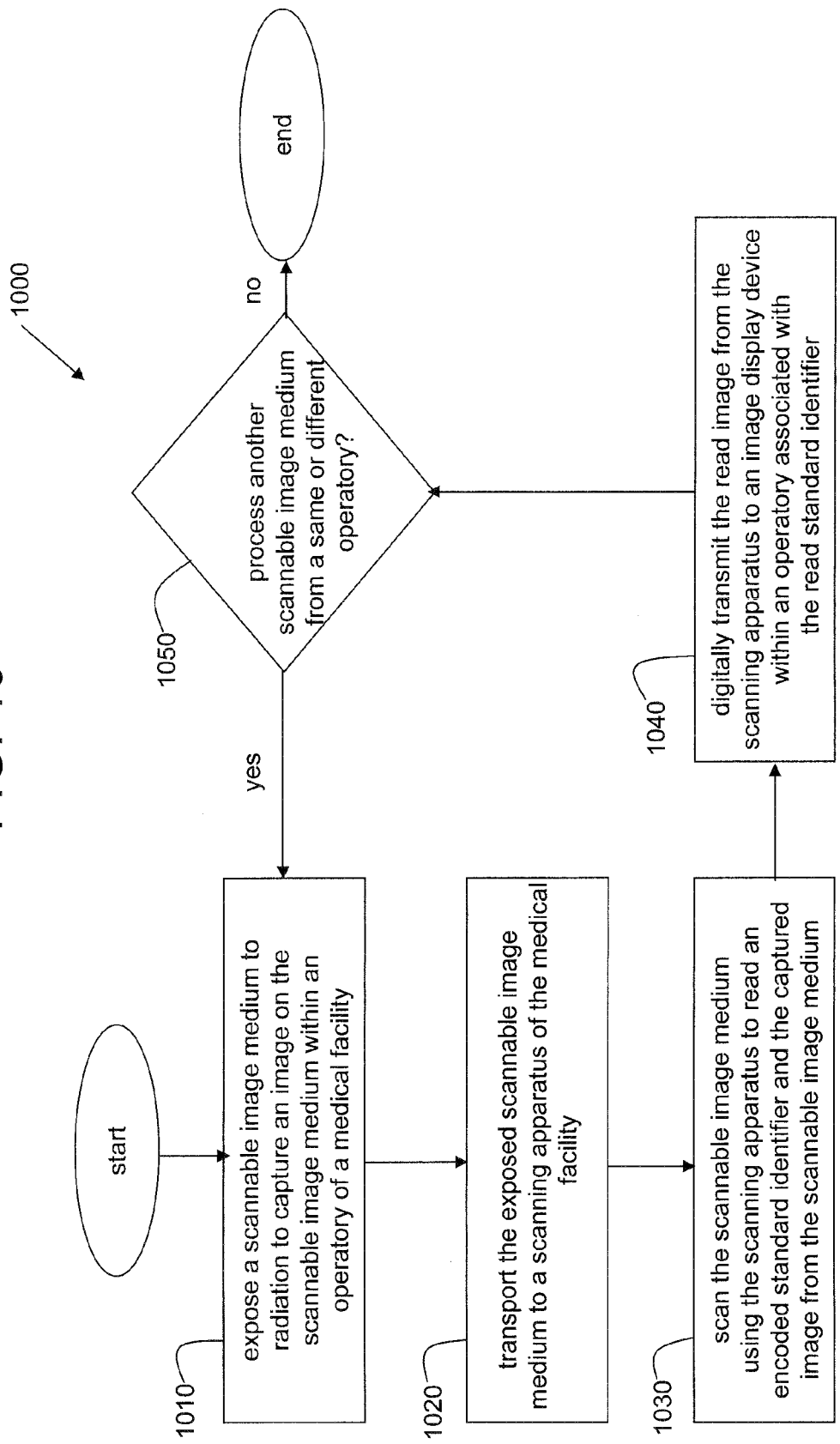

AUTO-DISTRIBUTION OF SCANNED DIGITAL IMAGES BASED ON STANDARDIZED IDENTIFIERS

TECHNICAL FIELD

Certain embodiments relate to digital radiography. More particularly, certain embodiments relate to the automatic distribution of scanned images from exposed media such as, for example, dental films based on standardized identifiers.

BACKGROUND

Various types of imaging systems are available for imaging the surface and/or the interior of such diverse entities such as, for example, the human anatomy, animals, man-made physical structures such as welding joints in bridges, geological formations, bodies of water, as well as many others. For example, in the field of dentistry, various types of intra-oral sensors exist which are used for capturing images of the inside of teeth and surrounding anatomy (e.g., bone structure) by exposing the anatomy and sensors to X-ray radiation. Such imaging techniques are well known using such intra-oral sensors as, for example, X-ray sensitive film, X-ray sensitive phosphor plates, or X-ray sensitive digital sensors such as a corded charge-coupled device (CCD) sensor, for example.

A medical facility may have many offices or operatories used for treating patients, including capturing images of certain anatomy of those patients for diagnostic purposes. For example, a dental facility may include several operatories where each operatory is equipped with a camera and/or an X-ray machine for taking inter-oral images of patients by a dental technician. The images are often captured on media such as radiographic film or photostimulable phosphor plates which are then scanned by a scanning apparatus somewhere within the dental facility to digitally extract the images from the media. Dental technicians from the various operatories typically use the same scanning apparatus, which may be located in a relatively central location of the dental facility, to scan the exposed media to create the digital images. The digital images may be saved on a disk that the dental technician can carry back to the operatory so the images may be viewed on a display device such as a personal computer by a dentist. However, a more efficient way of distributing scanned images within a medical facility is desirable.

Further limitations and disadvantages of conventional, traditional, and proposed approaches will become apparent to one of skill in the art, through comparison of such systems and methods with the subject matter of the present application as set forth in the remainder of the present application with reference to the drawings.

BRIEF SUMMARY

A first embodiment comprises a method to facilitate the automatic distribution of acquired images within a medical facility. The method includes encoding each of a first set of scannable image media with a same first standard identifier. The method further includes encoding each of a second set of scannable image media with a same second standard identifier. The method also includes electronically associating the first standard identifier with a first operatory or a first user computer within a medical facility. The method further includes electronically associating the second standard identifier with a second operatory or a second user computer within the medical facility. The encoding may be accomplished via one of radio frequency identification (RFID) (e.g., an RFID tag), optical encoding (e.g., holes within the media), magnetic encoding (e.g., a magnetic strip), and a bar code, for example. The scannable image media may include at least one of radiographic film, photographic film, and photostimulable phosphor plates, for example.

Another embodiment comprises a method to facilitate the automatic distribution of acquired images within a medical facility. The method includes placing a first set of scannable image media within a first operatory of a medical facility, wherein each of the first set of scannable image media is encoded with a same first standard identifier. The method further includes placing a second set of scannable image media within a second operatory of the medical facility, wherein each of the second set of scannable image media is encoded with a same second standard identifier. The method also includes electronically associating the first standard identifier with the first operatory within a scanning apparatus of the medical facility capable of scanning the scannable image media to read images and standard identifiers. The method further includes electronically associating the second standard identifier with the second operatory within the scanning apparatus. The scannable image media may include at least one of radiographic film, photographic film, and photostimulable phosphor plates. The encoded first standard identifier may reside in one of an RFID tag, an optical tag, a magnetic strip, or a bar code of each of the first set of scannable image media. Similarly, the encoded second standard identifier may reside in one of an RFID tag, an optical tag, a magnetic strip, or a bar code of each of the second set of scannable image media. The scanning apparatus may include at least one of a laser film scanner and a laser phosphor plate scanner. Furthermore, the scanning apparatus may include at least one of an RFID reader, an optical code reader, a magnetic code reader, and a bar code reader.

A further embodiment comprises a method of processing scannable image media within a medical facility. The method includes scanning a first scannable image medium, encoded with a first standard identifier and storing a first image, using a scanning apparatus within a medical facility to read the first standard identifier and the first image from the first scannable image medium. The method further includes scanning a second scannable image medium, encoded with a second standard identifier and storing a second image, using the scanning apparatus to read the second standard identifier and the second image from the second scannable image medium. The method also includes digitally transmitting the read first image from the scanning apparatus to a first image display device within a first operatory of the medical facility in response to the read first standard identifier. The method further includes digitally transmitting the read second image from the scanning apparatus to a second image display device within a second operatory of the medical facility in response to the read second standard identifier. The first and second scannable image media may each include one of a radiographic film, a photographic film, and a photostimulable phosphor plate. The encoded first standard identifier may reside in one of an RFID tag, an optical tag, a magnetic strip, or a bar code on the first scannable image medium. Similarly, the encoded second standard identifier may reside in one of an RFID tag, an optical tag, a magnetic strip, or a bar code on the second scannable image medium. The scanning apparatus may include at least one of a laser film scanner and a laser phosphor plate scanner. Furthermore, the scanning apparatus may include at least one of an RFID reader, an optical code reader, a magnetic code reader, and a bar code reader.

Another embodiment comprises a method of acquiring and distributing images within a medical facility. The method includes exposing a first scannable image medium to X-ray radiation to capture a first image on the first scannable image medium within a first operatory of the medical facility. The method further includes transporting the first scannable image medium to a scanning apparatus of the medical facility. The method also includes scanning the first scannable image medium using the scanning apparatus to read a first encoded standard identifier and the captured first image from the scannable image medium. The method further includes digitally transmitting the read first image from the scanning apparatus to a first image display device within the first operatory in response to the read first standard identifier. The method may further include exposing a second scannable image medium to X-ray radiation to capture a second image on the second scannable image medium within a second operatory of the medical facility. The method may also include transporting the second scannable image medium to the scanning apparatus of the medical facility. The method may further include scanning the second laser scannable image medium using the scanning apparatus to read a second encoded standard identifier and the captured second image from the second scannable image medium. The method may also include digitally transmitting the read second image from the scanning apparatus to a second image display device within the second operatory in response to the read second standard identifier. The first and the second scannable image media may each include one of a radiographic film, a photographic film, and a photostimulable phosphor plate. The first encoded standard identifier may reside in one of an RFID tag, an optical tag, a magnetic strip, or a bar code of the first scannable image medium. Similarly, the second encoded standard identifier may reside in one of an RFID tag, an optical tag, a magnetic strip, or a bar code of the second scannable image medium. The scanning apparatus may include at least one of a laser film scanner and a laser phosphor plate scanner. Furthermore, the scanning apparatus may include at least one of an RFID reader, an optical code reader, a magnetic code reader, and a bar code reader.

An additional embodiment comprises a system to facilitate the automatic distribution of acquired images within a medical facility. The system includes means for displaying digital images within a first operatory of a medical facility and means for displaying digital images within a second operatory of a medical facility. The system further includes means for scanning a scannable image medium to read an encoded identifier and a captured image from the scannable image medium, wherein the encoded identifier is associated with the first operatory or the second operatory. The system also includes means for transmitting the read image to the means for displaying digital images within the first operatory or to the means for displaying digital images within the second operatory in dependence on the read associated identifier. The system may further include means for capturing an image on the scannable image medium within the first operatory, and means for capturing an image on the scannable image medium within the second operatory. The scannable image medium may include one of a radiographic film, a photographic film, and a photostimulable phosphor plate.

These and other novel features of the subject matter of the present application, as well as details of illustrated embodiments thereof, will be more fully understood from the following description and drawings.

BRIEF DESCRIPTION OF THE DRAWINGS

FIG. 10 illustrates a flow chart of an exemplary embodiment of a method of acquiring and distributing images within a medical facility.

DETAILED DESCRIPTION

The following description is presented in the context of intra-oral imaging for the field of dentistry. However, various embodiments may be applied to other imaging fields as well such as, for example, other branches of medical imaging.

Figure 1:
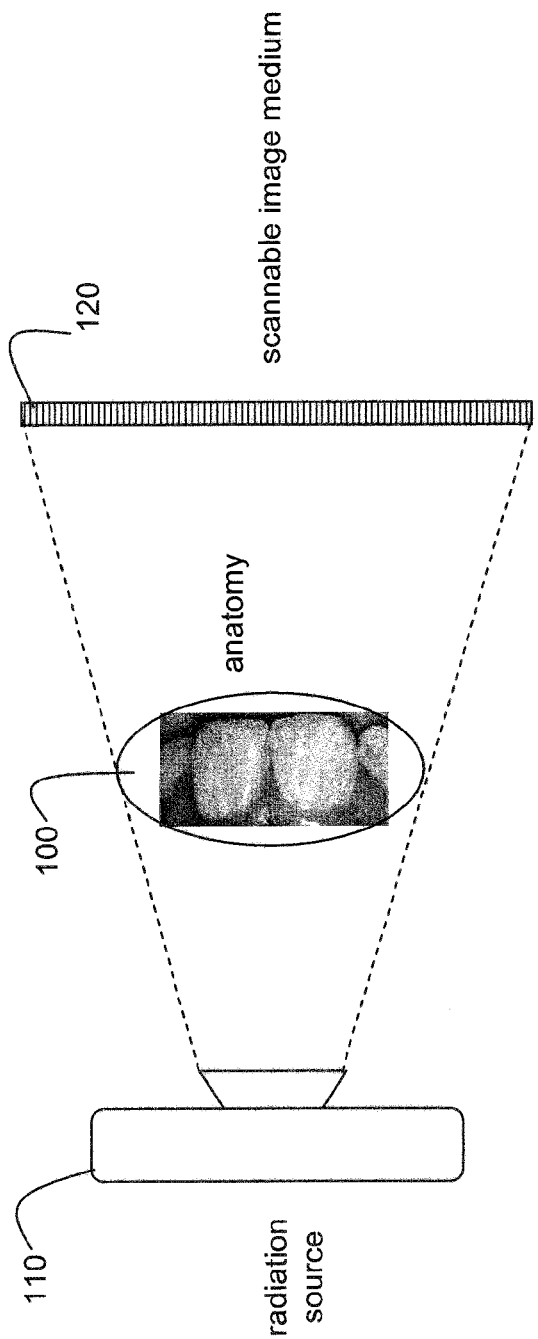
FIG. 1 illustrates a schematic diagram of an exemplary embodiment of a process for capturing an image of an anatomical structure using a radiation source and a scannable image medium.

FIG. 1 illustrates a schematic diagram of an exemplary embodiment of a process for capturing an image of an anatomical structure 100 using a radiation source 110 (e.g., an X-ray tube) and a scannable image medium 120 (e.g., a photostimulable phosphor plate). The X-ray tube 110 emits a dose of X-ray radiation toward the anatomical structure 100. Some of the X-ray radiation passes through the anatomical structure 100 and exposes the scannable image medium 120, capturing an image of the anatomical structure 100 on the image medium 120. In accordance with various embodiments, the scannable image medium may include one of a radiographic film, a photosensitive film, or a photostimulable phosphor plate which are well known in the art. Other scannable image media may be possible as well.

Figure 2:
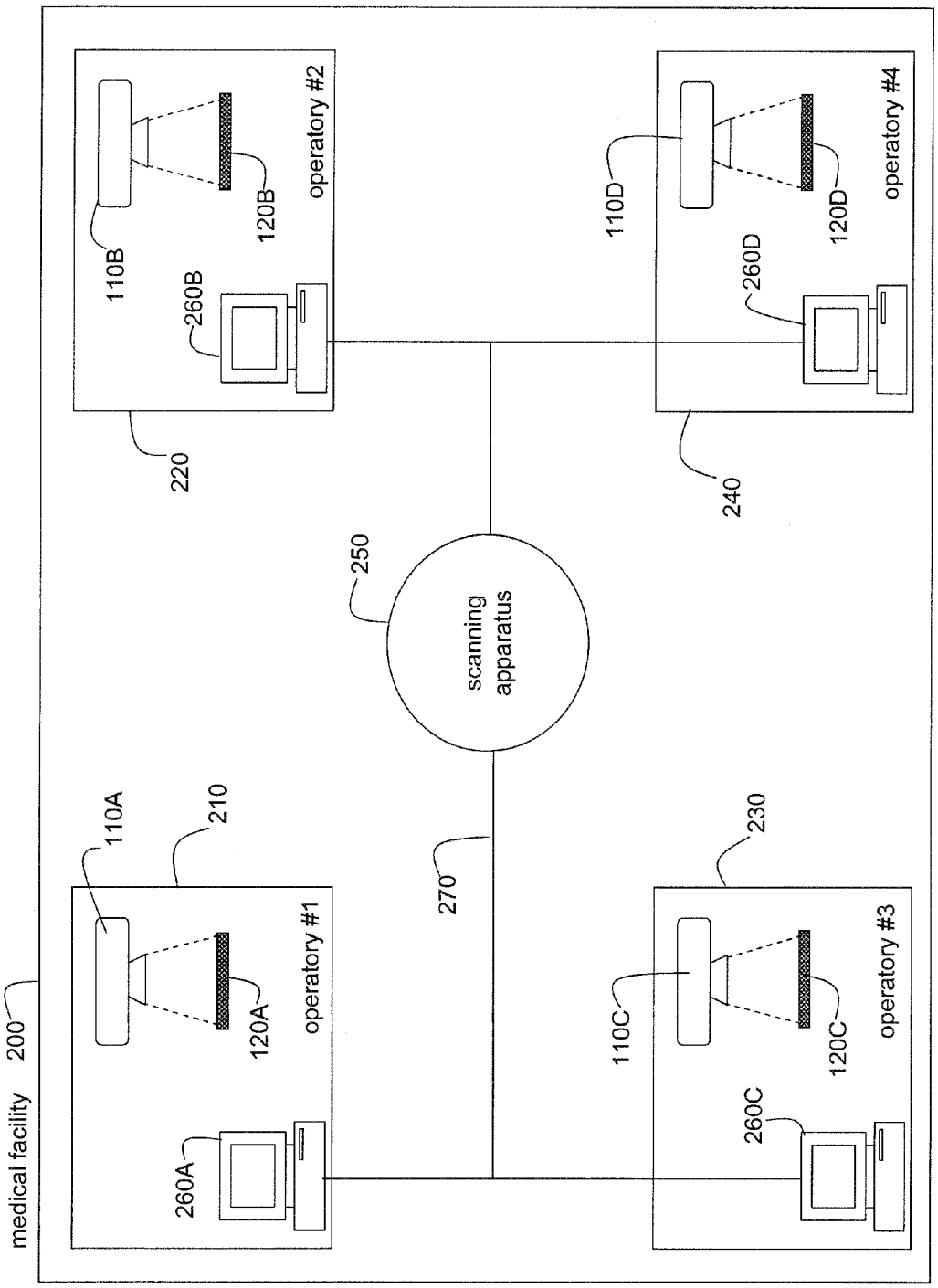
FIG. 2 illustrates a schematic diagram of an exemplary embodiment of a medical facility having a plurality of operatories and a scanning apparatus.

FIG. 2 illustrates a schematic diagram of an exemplary embodiment of a medical facility 200 having a plurality of operatories (e.g., 210, 220, 230, and 240) and a scanning apparatus 250. The operatories are used for capturing images of patient anatomical structures on scannable image media (e.g., 120A-D). Each operatory includes a radiation source (e.g., 110A-D) and an image display device (e.g., 260A-D) for viewing images. For example, in accordance with an embodiment, the medical facility may comprise a dental facility where the operatories are used for capturing intra-oral images from patient anatomical structures (e.g., teeth) on the scannable image media. The radiation sources may include X-ray machines and the image display devices may include personal computers, for example. The scannable image media may include radiographic films or photostimulable phosphor plates, for example.

The scanning apparatus 250 is capable of scanning the image media to digitally extract a captured image from the image media. Furthermore, in accordance with an embodiment, each scannable image medium is encoded with a standard identifier and the scanning apparatus 250 is capable of reading the standard identifier of any scannable image medium. Such capabilities are explained in further detail herein with respect to FIGS. 3-10. The encoded standard identifier is associated with a particular operatory of the medical facility and/or a particular image display device (e.g., a personal computer or workstation) within an operatory. A first plurality of scannable image media may have the same first encoded standard identifier because that first plurality of scannable image media is intended to be used within a same particular first operatory, for example. Similarly, a second plurality of scannable image media may have the same second encoded standard identifier because that second plurality of scannable image media is intended to be used within a same particular second operatory, for example.

Figure 3:
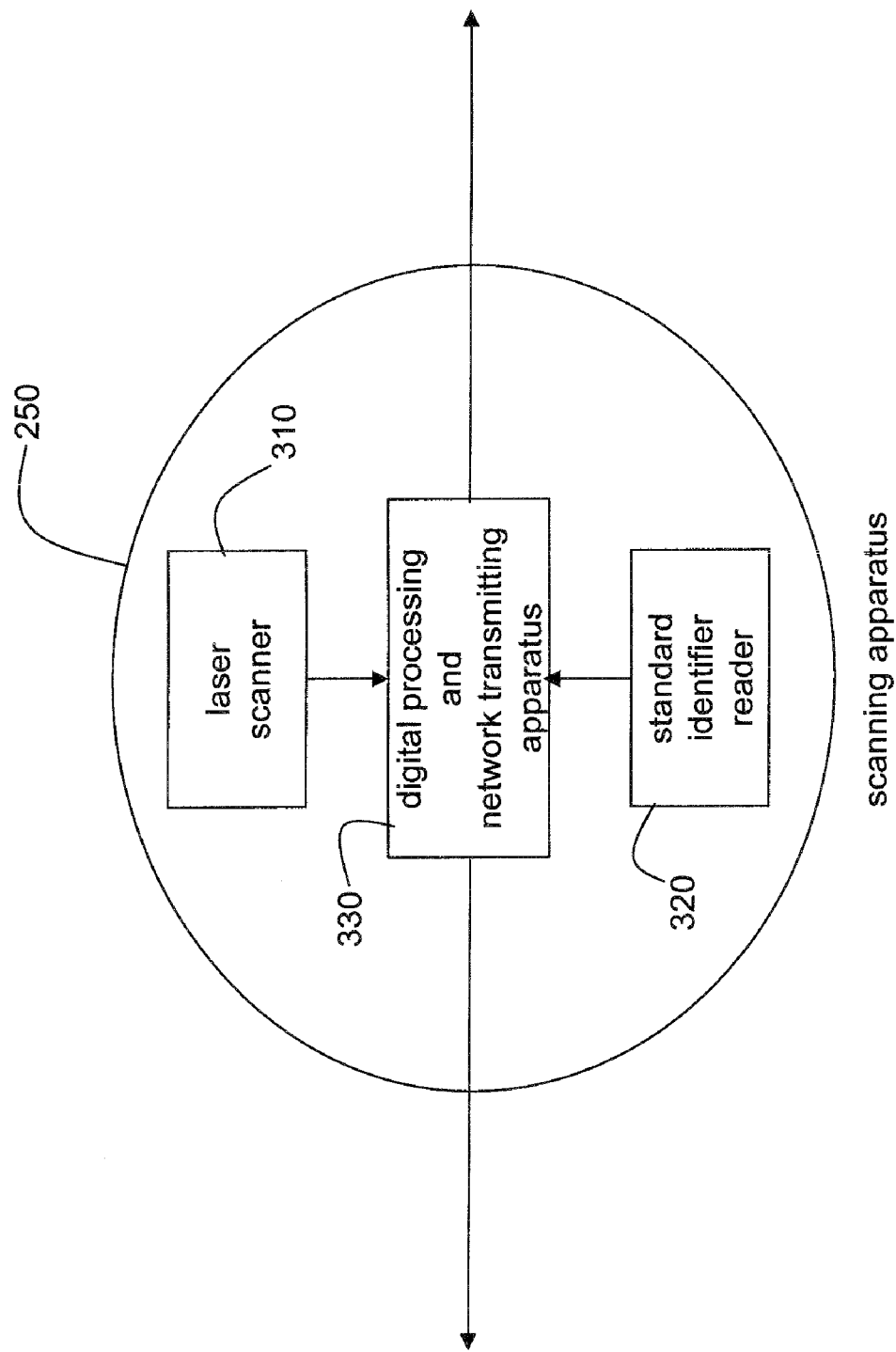
FIG. 3 illustrates a schematic block diagram of an exemplary embodiment of the scanning apparatus of FIG. 2 including a laser scanner and a standard identifier reader.

FIG. 3 illustrates a schematic block diagram of an exemplary embodiment of the scanning apparatus 250 of FIG. 2 including a laser scanner 310 and a standard identifier reader 320. The scanning device 250 also includes a digital processing and network transmitting apparatus 230 which is operationally connected to the laser scanner 310 and the standard identifier reader 320. The laser scanner 310 is capable of scanning an image from a scannable image medium (e.g., a radiographic film or a photostimulable phosphor plate) to extract a digital image. The laser scanner 310 may be configured to scan a photostimulable phosphor plate (see FIG. 4) or a radiographic film (see FIG. 5) in accordance with various embodiments. Also, the standard identifier reader 320 is capable of reading an encoded standard identifier on a scannable image medium. The standard identifier reader 320 may be configured as an RFID reader, an optical reader, a magnetic reader, or a bar code reader in accordance with various embodiments. Other types of readers may be possible as well, in accordance with various embodiments. A user places a scannable image medium into the scanning apparatus 250 to have both the exposed image and the standard identifier read by the laser scanner 310 and the standard identifier reader 320, respectively. The scanning apparatus 250 is operationally connected to the image display devices (260A-260D) of the operatories (210-240) via a network 270 (wired or wireless) such as, for example, a local area network (LAN).

Figure 4:
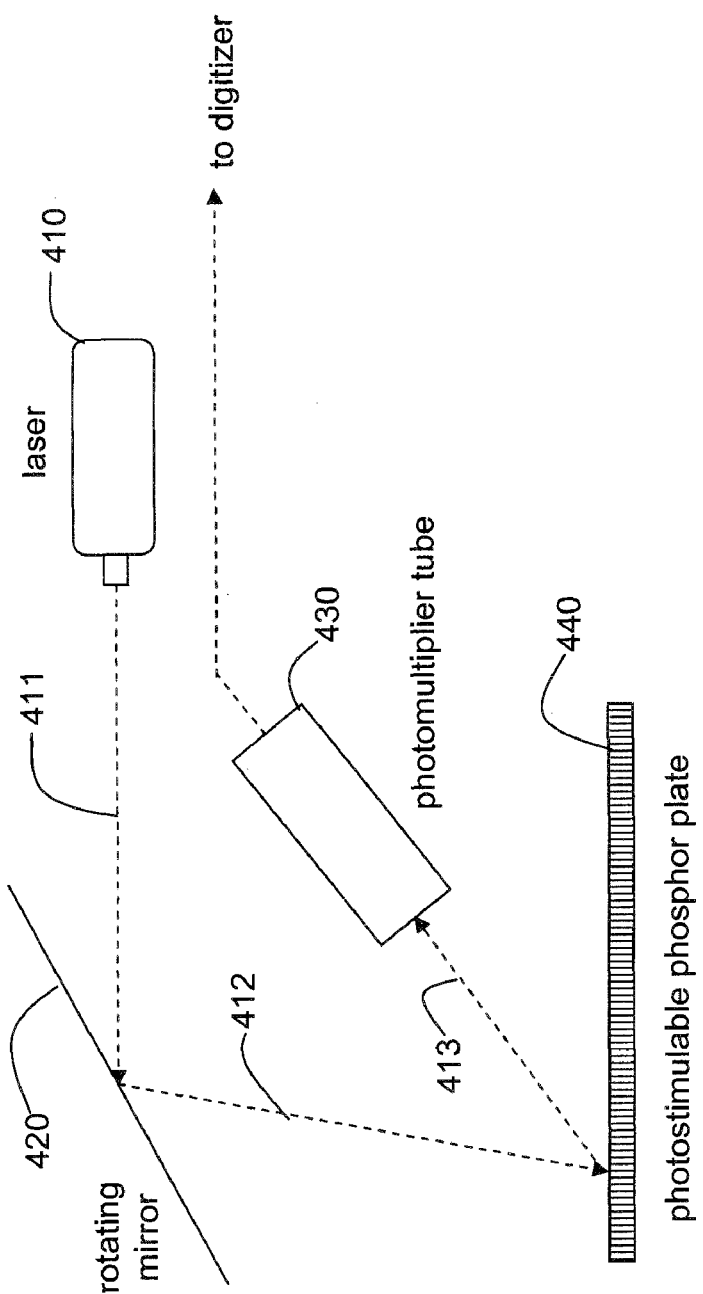
FIG. 4 illustrates a schematic block diagram of a first exemplary embodiment of the laser scanner of FIG. 3.

FIG. 4 illustrates a schematic block diagram of a first exemplary embodiment of the laser scanner 310 of FIG. 3. The laser scanner 310 includes a laser source 410, a rotating mirror 420, and a photomultiplier tube 430. When scanning, for example, a photostimulable phosphor plate 440, the laser source 410 emits a laser beam 411 toward the rotating mirror 420 which reflects the laser beam toward the photostimulable phosphor plate 440. The reflected laser beam 412 interacts with the photostimulable phosphor plate 440 causing light 413, representative of image pixels, to be directed toward the photomultiplier tube 430. As the mirror 420 rotates, the entire exposed surface of the photostimulable phosphor plate 440 is illuminated and scanned in this manner to extract all of the associated image pixels. The photomultiplier tube 430 amplifies the light associated with the image pixels as scanning proceeds and converts the light to analog electrical signals. The analog electrical signals may then be passed on to a digitizer operationally connected to an output of the photomulitplier tube 430 to convert the analog electrical signals to digital electrical signals, to form digital pixel image data. Such a digitizer may be part of the laser scanner 310, or may be part of the digital processing and network transmitting apparatus 330, in accordance with various embodiments. Such laser scanners are well known in the art.

Figure 5:
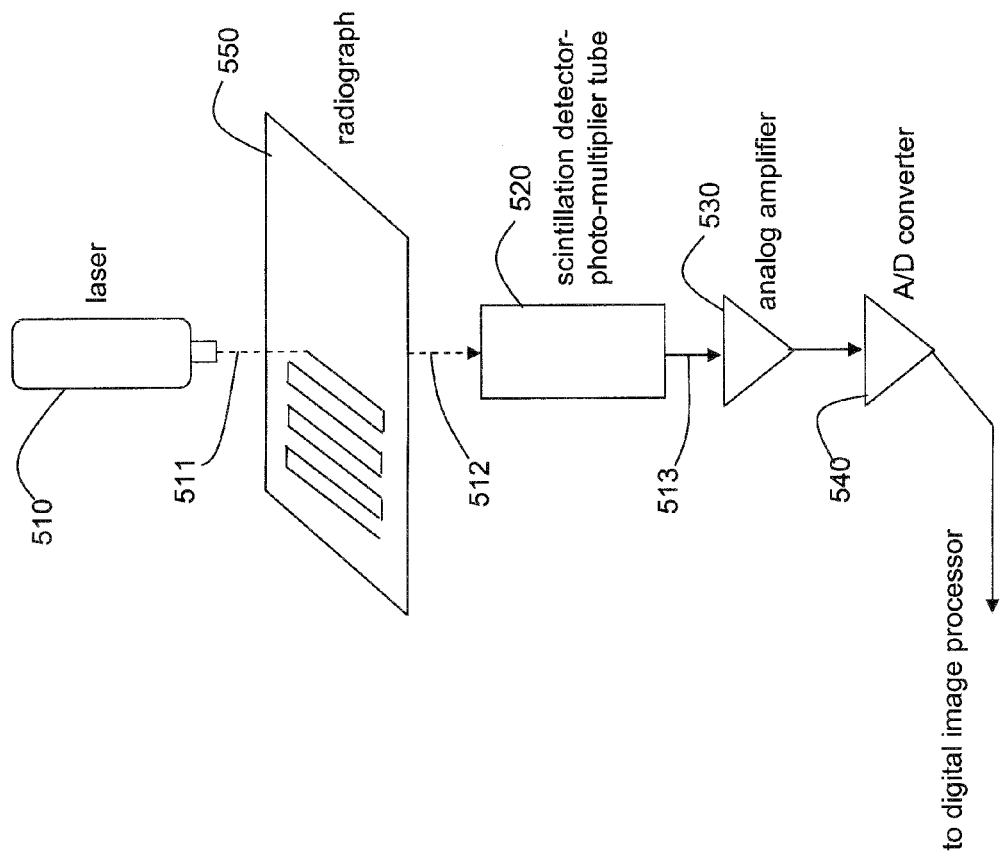
FIG. 5 illustrates a schematic block diagram of a second exemplary embodiment of the laser scanner of FIG. 3.

FIG. 5 illustrates a schematic block diagram of a second exemplary embodiment of the laser scanner 310 of FIG. 3. The laser scanner 310 includes a laser source 510, a scintillation detector-photomultiplier tube 520, an analog amplifier 530 operationally connected to an output of the tube 520, and an analog-to-digital (A/D) converter 540 operationally connected to an output of the analog amplifier 530. When scanning, for example, a radiographic film 550, the laser source 510 emits a laser beam 511 toward the radiographic film 550. The laser beam passes through the film 550 and is modulated by the recorded image on the radiographic film 550. The laser source may be mounted on a motor assembly which scans the laser beam 511 across the radiograph 550. Alternatively, a rotating mirror may be employed in a manner similar to that of FIG. 4.

The modulated beam of light 512 is received by the tube 520 which amplifies the modulated beam of light and converts the modulated beam of light to analog electrical signals 513. The analog electrical signals 513 are amplified by the analog amplifier 530 which is operationally connected to the photomultiplier tube 520. The amplified analog signals are then converted to digital signals by the A/D converter 540 which is operationally connected to the analog amplifier 530 to form digital pixel image data. The digital pixel image data may then be passed to the digital processing and network transmitting apparatus 330 of the scanner apparatus 250 serving, at least in part, as an image processor. Such laser scanners are well known in the art.

Figure 6:
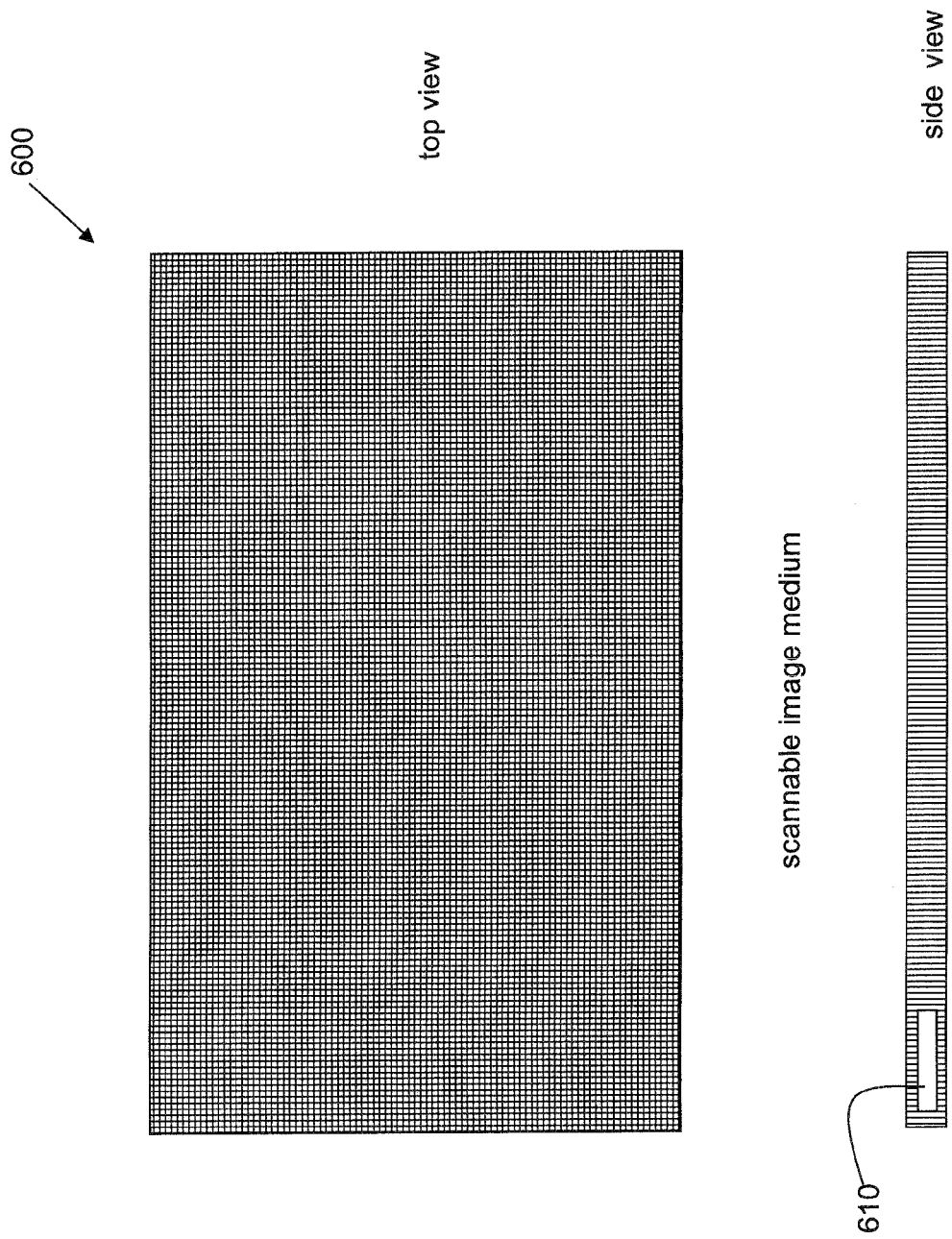
FIG. 6 illustrates a schematic diagram of an exemplary embodiment of a scannable image medium having an RFID tag encoded with a standard identifier.
Figure 7:
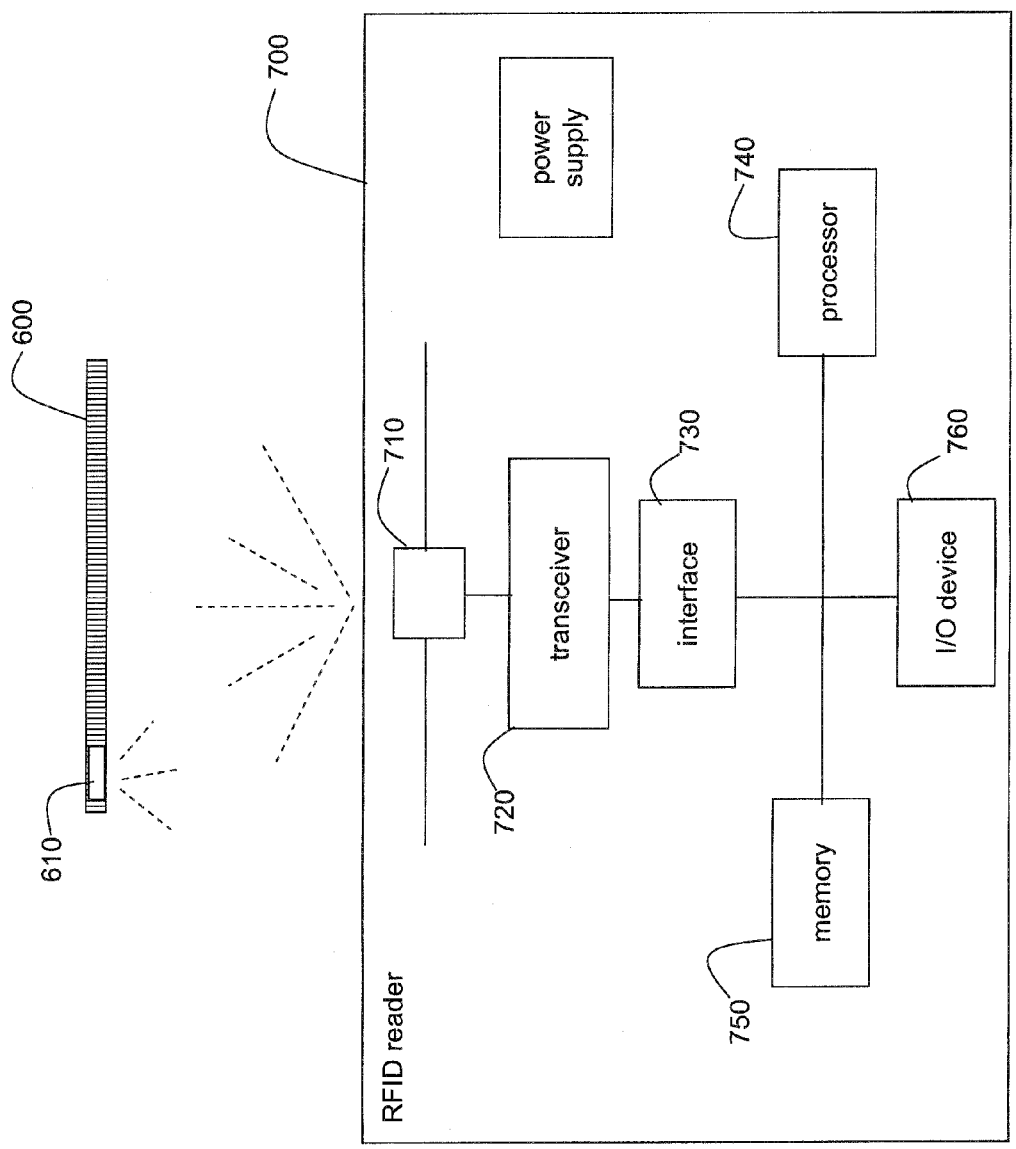
FIG. 7 illustrates a schematic block diagram of an exemplary embodiment of the standard identifier reader of FIG. 3 as being an RFID reader, and an exemplary embodiment of a process for reading the RFID tag of the scannable image medium of FIG. 6.

FIG. 6 illustrates a schematic diagram of an exemplary embodiment of a scannable image medium 600 having an RFID tag 610 encoded with a standard identifier. FIG. 7 illustrates a schematic block diagram of an exemplary embodiment of the standard identifier reader 320 of FIG. 3 as being an RFID reader 700, and an exemplary embodiment of a process for reading the RFID tag 610 of the scannable image medium 600 of FIG. 6.

The RFID reader 700 includes an antenna 710 and a transceiver 720 operationally connected to the antenna 710. The RFID reader 700 further includes an interface 730 operationally connected to the transceiver 720. The interface 730 may serve, at least in part, as a signal sampling unit and an A/D converter, for example. The RFID reader also includes a processor 740, a memory 750, and an input/output (I/O) device 760 operationally connected to each other and to the interface 730. The RFID reader 700 also includes a power supply 770 to supply power to the various elements of the RFID reader 700. Such RFID readers are well known in the art.

When a scannable image medium 600 (e.g., a photostimulable phosphor plate) having an encoded RFID tag is placed into the scanning apparatus 250. The standard identifier reader 320 (being the RFID reader 700) interrogates the RFID tag 610 via an RF energy signal generated by the transceiver 720 and transmitted toward the RFID tag 610 via the antenna 710. Upon receiving the RF energy signal, the RFID tag 610 responds by transmitting back an RF energy signal representative of the standard identifier encoded in the RFID tag 610. The transceiver 720 of the RFID reader 700 receives the RF signal from the RFID tag 610 via the antenna 710 and the processor 740 processes the signal to form the digital standard identifier which may be stored in memory 750 and/or forwarded to the digital processing and network transmitting apparatus 330 of the scanning apparatus 250 as the standard identifier of the scannable image medium 600.

Figure 8:
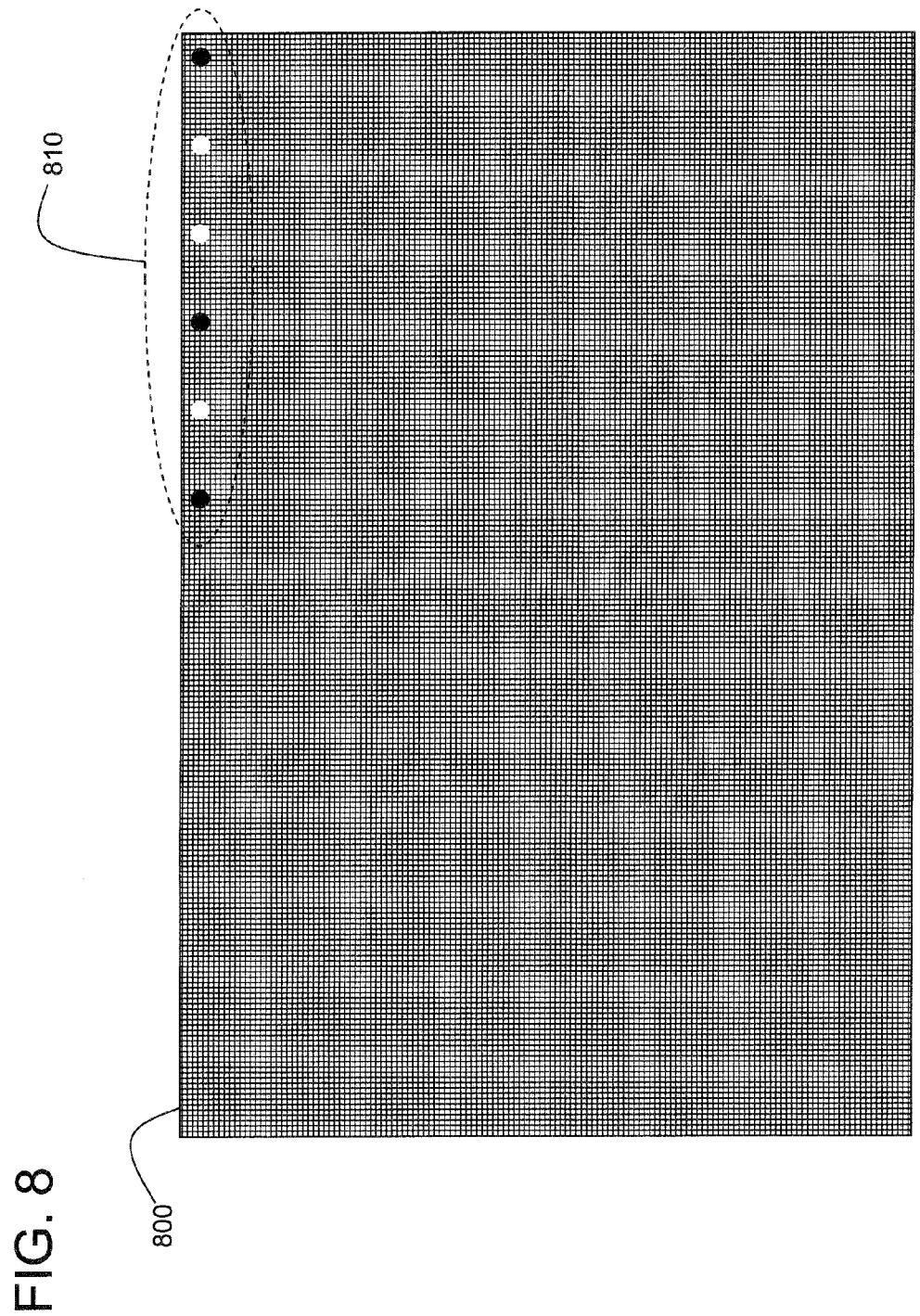
FIG. 8 illustrates a schematic diagram of an exemplary embodiment of a scannable image medium having an optical code encoding a standard identifier.

FIG. 8 illustrates a schematic diagram of an exemplary embodiment of a scannable image medium 800 having an optical code 810 encoding a standard identifier. The optical code 810 is formed by open holes and filled holes along the edge of the scannable image medium 800. For example, the open and filled holes 810 shown in FIG. 8 represent the digital code "010110" as read from left to right, where an open hole represents a "1" and a filled hole represents a "0".

Figure 9:
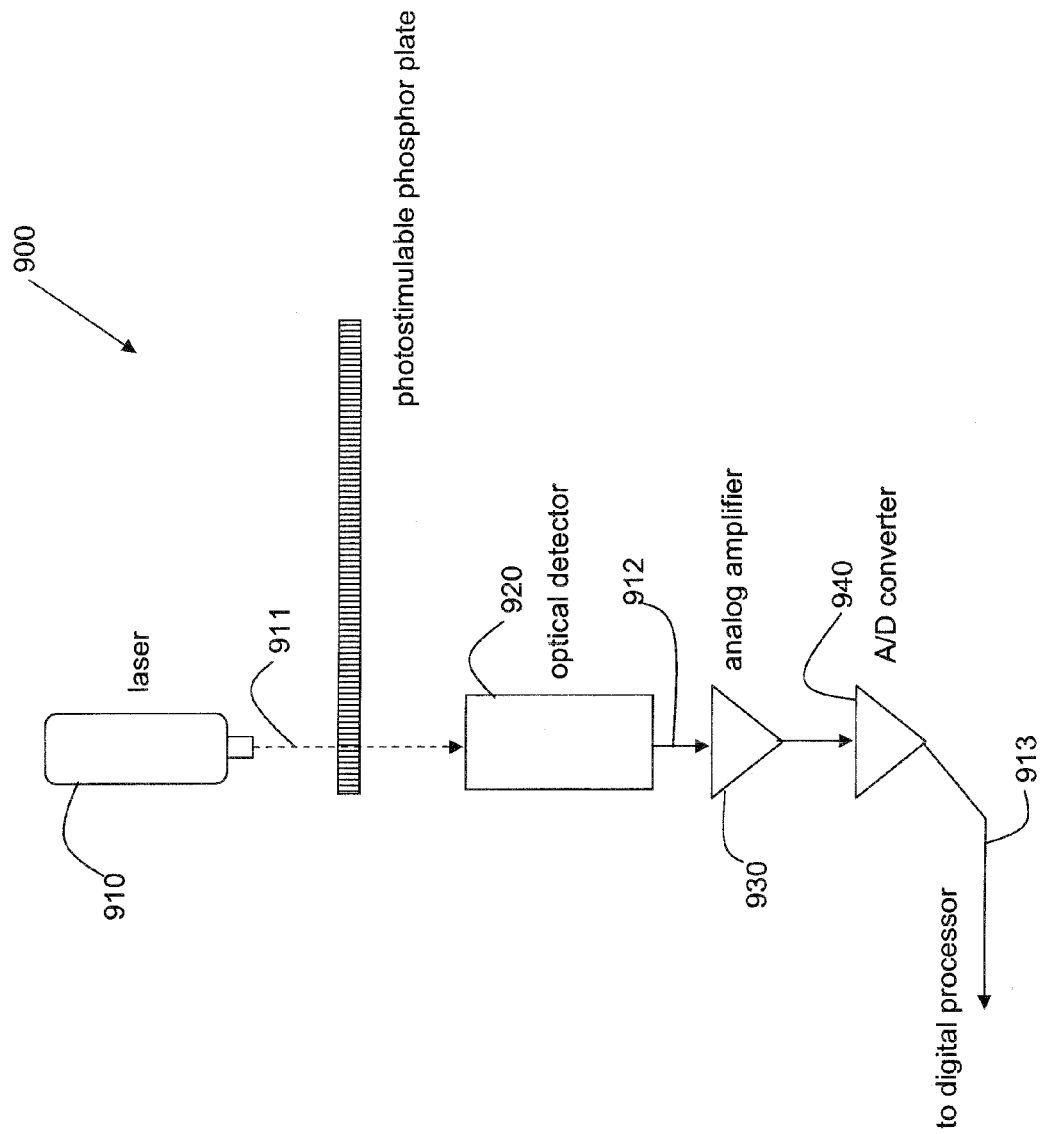
FIG. 9 illustrates a schematic block diagram of an exemplary embodiment of the standard identifier reader of FIG. 3 as being an optical reader, and an exemplary embodiment of a process for reading the optical code of the scannable image medium of FIG. 8.

FIG. 9 illustrates a schematic block diagram of an exemplary embodiment of the standard identifier reader 320 of FIG. 3 as being an optical reader 900, and an exemplary embodiment of a process for reading the optical code 810 of the scannable image medium 800 of FIG. 8. The optical reader 900 includes a laser source 910 which is used to scan the open and filled holes forming the optical code 810 of the image medium 800 (e.g., a photostimulable phosphor plate).

The optical reader 900 also includes an optical detector 920. When scanning the optical code 810 of a scannable image medium placed in the scanning apparatus 250, a laser beam 911 emitted from the laser source 910 passes through a hole of the code 810 and is received at the optical detector 920, representing a digital "1" of the code 810. When the laser beam 911 scans over a filled hole, the optical detector 920 does not receive the laser beam 911, representing a digital "0" of the code 810. In this manner, the entire optical code 810 formed by the open and filled holes of the scannable image medium 800 may be read. The optical detector 920 converts the received light beam 911 (or lack thereof) to an analog electrical signal 912. The laser source may be mounted on a motor assembly which scans the laser beam 911 across the open and filled holes. Alternatively, a rotating mirror may be employed in a manner similar to that of FIG. 4.

The optical reader 900 includes an analog amplifier 930 operationally connected to an output of the optical detector 920 to receive the analog electrical signal 912 and amplify the analog electrical signal 912. The optical reader further includes an A/D converter 940 operationally connected to the output of the analog amplifier 930 to receive and convert the amplified analog electrical signal to a digital electrical signal 913. The digital electrical signals 913, corresponding to each of the open and filled holes of the optical code 810, may be forwarded to the digital processing and network transmitting apparatus 330 of the scanning apparatus 250 as the standard identifier of the scannable image medium 800.

FIG. 10 illustrates a flow chart of an exemplary embodiment of a method 1000 of acquiring and distributing images within a medical facility 200. In step 1010, expose a scannable image medium 120A to X-ray radiation to capture an image on the scannable image medium 120A within an operatory 210 of the medical facility 200. In step 1020, transport the exposed scannable image medium 120A to a scanning apparatus 250 of the medical facility 200. In step 1030, scan the image medium 120A using the scanning apparatus 250 to read an encoded standard identifier and the captured image from the scannable image medium 120A. In step 1040, digitally transmit the read image from the scanning apparatus 250 to an image display device 260A within an operatory 210 associated with the read standard identifier. In step 1050, if there is another scannable image medium 120D to be scanned, from a same or different operatory 240, then proceed to step 1010. Otherwise, end the method 1000.

As a result, scannable image media, each having an encoded standard identifier which is associated with a particular operatory or image display device within a particular operatory, may be scanned to read the digital image data and the standard identifier. The standard identifier is used by the scanning apparatus to automatically transmit the read digital image to the appropriate image display device within the appropriate operatory.

For example, referring to FIG. 3, the read image data is provided to the digital processing and network transmitting apparatus 330 from the laser scanner 310. Also, the read standard identifier is provided to the digital processing and network transmitting apparatus 330 from the standard identifier reader 320. The digital processing and network transmitting apparatus 330 formats the image data, if needed, and automatically digitally transmits the image data to the appropriate image display device within the appropriate operatory, based on the standard identifier, via a network of the medical facility.

The digital processing and network transmitting apparatus 330 is configured in advanced to associate particular standard identifiers with particular operatories, or image display devices (e.g., PC's) within those particular operatories. For example, the table below maps standard identifiers to particular operatories of FIG. 2:

| STANDARD IDENTIFIER | OPERATORY |
|---|---|
| 001 | 210 |
| 010 | 220 |
| 011 | 230 |
| 100 | 240 |

As long as users within a particular operatory use only scannable image media having a same standard code, then whenever such scannable image media is scanned by the scanning apparatus 250, the resultant read digital images will automatically be transferred back to the same operatory. Such systems and methods result in improved efficiencies within a medical facility.

As an example, referring to FIG. 2, a medical facility 200 may receive several sets of scannable image media which are capable of being encoded with a standard identifier at the medical facility 200 (e.g., by punching out certain punch holes in a radiographic film to form an optical code). Each of a first set of scannable image media may be encoded with a same first standard identifier (to be used in a first operatory 210), and each of a second set of scannable image media may be encoded with a same second standard identifier (to be used in a second operatory 240). The first standard identifier is electronically associated with the first operatory 210 or a first user computer 260A within the medical facility 200 (e.g., by programming the scanning apparatus 250 to make such an association). Also, the second standard identifier is electronically associated with the second operatory 240 or a second user computer 260D within the medical facility 200 (e.g., by programming the scanning apparatus 250 to make such an association).

The first set of scannable image media may be placed in the first operatory 210 of the medical facility 200 and the second set of image media may be placed in the second operatory 240 of the medical facility 200 for use within those respective operatories. As an example, a user (e.g., a dental technician)

within the first operatory 210 may take a first scannable image medium 120A (e.g., a radiographic film), which has been encoded with a first standard identifier and exposed to capture an image, to the scanning apparatus 250 to be read. Similarly, a user (e.g., a dental technician) within the second operatory 240 may take a second scannable image medium 120D (e.g., a radiographic film), which has been encoded with a second standard identifier and exposed to capture an image, to the scanning apparatus 250 to be read.

The scanning apparatus 250 reads the image and the standard identifier, as described previously herein, from the first scannable image medium 120A and the second scannable image medium 120D and transmits the first read image from the scanning apparatus 250 to a first image display device 260A within the first operatory 210 in response to the first read standard identifier and, similarly, transmits the second read image from the scanning apparatus 250 to a second image display device 260D within the second operatory 240 in response to the second read standard identifier.

As a result, the users do not have to think about getting the read image back to the correct operatory (e.g., by saving the scanned image to a disk and carrying the disk back to the operatory, or by manually telling the scanning apparatus 250 where to send a particular read image). The scanning apparatus 250 automatically transmits a particular scanned image to the correct operatory for viewing by, for example, a dentist based on the read standard identifier of the corresponding scannable image medium. Therefore, the operational efficiency of the dental facility is increased.

In summary, a system and methods for facilitating the automatic distribution of acquired images within a medical facility is disclosed. Means for displaying digital images within two or more operatories is provided. Means for scanning scannable image media is also provided, to read an encoded identifier and a captured image from each of the scannable image media. The encoded identifier of any given scannable image medium is associated with one operatory of the medical facility. Means for transmitting a read image to the means for displaying digital images within a particular operatory in dependence on the read associated identifier is further provided.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiment disclosed, but that the claimed subject matter will include all embodiments falling within the scope of the appended claims.

What is claimed is:

1. A method to facilitate the automatic distribution of acquired images within a medical facility, said method comprising:
   encoding each of a first set of scannable image media with a same first standard identifier;
   encoding each of a second set of scannable image media with a same second standard identifier;
   electronically associating said first standard identifier with a first operatory or a first user computer within a medical facility; and
   electronically associating said second standard identifier with a second operatory or a second user computer within said medical facility.

2. The method of claim 1 wherein said encoding is accomplished via one of radio frequency identification (RFID), optical encoding, magnetic encoding, and bar coding.

3. The method of claim 1 wherein said scannable image media include at least one of radiographic film, photographic film, and photostimulable phosphor plates.

4. A method to facilitate the automatic distribution of acquired images within a medical facility, said method comprising:
   placing a first set of scannable image media within a first operatory of a medical facility, wherein each of said first set of scannable image media is encoded with a same first standard identifier;
   placing a second set of scannable image media within a second operatory of said medical facility, wherein each of said second set of scannable image media is encoded with a same second standard identifier;
   electronically associating said first standard identifier with said first operatory within a scanning apparatus of said medical facility capable of scanning said scannable image media to read images and standard identifiers; and
   electronically associating said second standard identifier with said second operatory within said scanning apparatus.

5. The method of claim 4 wherein said scannable image media include at least one of radiographic film, photographic film, and photostimulable phosphor plates.

6. The method of claim 4 wherein said encoded first standard identifier resides in one of a radio frequency identification (RFID) tag, an optical tag, a magnetic strip, or a bar code of each of said first set of scannable image media.

7. The method of claim 4 wherein said encoded second standard identifier resides in one of a radio frequency identification (RFID) tag, an optical tag, a magnetic strip, or a bar code of each of said second set of scannable image media.

8. The method of claim 4 wherein said scanning apparatus includes at least one of a laser film scanner and a laser phosphor plate scanner.

9. The method of claim 4 wherein said scanning apparatus includes at least one of an RFID reader, an optical reader, a magnetic reader, and a bar code reader.

10. A method of processing scannable image media within a medical facility, said method comprising:
    scanning a first scannable image medium, encoded with a first standard identifier and storing a first image, using a scanning apparatus within a medical facility to read said first standard identifier and said first image from said first scannable image medium;
    scanning a second scannable image medium, encoded with a second standard identifier and storing a second image, using said scanning apparatus to read said second standard identifier and said second image from said second scannable image medium;
    digitally transmitting said read first image from said scanning apparatus to a first image display device within a first operatory of said medical facility in response to said read first standard identifier; and
    digitally transmitting said read second image from said scanning apparatus to a second image display device within a second operatory of said medical facility in response to said read second standard identifier.

11. The method of claim 10 wherein said first and second scannable image media each include one of a radiographic film, a photographic film, and a photo stimulable phosphor plate.

12. The method of claim 10 wherein said encoded first standard identifier resides in one of a RFID tag, an optical tag, a magnetic strip, or a bar code on said first scannable image medium.

13. The method of claim 10 wherein said encoded second standard identifier resides in one of a RFID tag, an optical tag, a magnetic strip, or a bar code on said second scannable image medium.

14. The method of claim 10 wherein said scanning apparatus includes at least one of a laser film scanner and a laser phosphor plate scanner.

15. The method of claim 10 wherein said scanning apparatus includes at least one of an RFID reader, an optical reader, a magnetic reader, and a bar code reader.

16. A method of acquiring and distributing images within a medical facility, said method comprising:
    exposing a first scannable image medium to radiation to capture a first image on said first scannable image medium within a first operatory of a medical facility;
    transporting said first scannable image medium to a scanning apparatus of said medical facility;
    scanning said first scannable image medium using said scanning apparatus to read a first encoded standard identifier and said captured first image from said first scannable image medium; and
    digitally transmitting said read first image from said scanning apparatus to a first image display device within said first operatory in response to said read first standard identifier.

17. The method of claim 16 further comprising:
    exposing a second scannable image medium to radiation to capture a second image on said second scannable image medium within a second operatory of said medical facility;
    transporting said second scannable image medium to said scanning apparatus of said medical facility;
    scanning said second scannable image medium using said scanning apparatus to read a second encoded standard identifier and said captured second image from said second scannable image medium; and
    digitally transmitting said read second image from said scanning apparatus to a second image display device within said second operatory in response to said read second standard identifier.

18. The method of claim 17 wherein said first and second scannable image media each include one of a radiographic film, a photographic film, and a photo stimulable phosphor plate.

19. The method of claim 16 wherein said first encoded standard identifier resides in one of a RFID tag, an optical tag, a magnetic strip, or a bar code on said first scannable image medium.

20. The method of claim 17 wherein said second encoded standard identifier resides in one of a RFID tag, an optical tag, a magnetic strip, or a bar code on said second scannable image medium.

21. The method of claim 17 wherein said scanning apparatus includes at least one of a laser film scanner and a laser phosphor plate scanner.

22. The method of claim 17 wherein said scanning apparatus includes at least one of an RFID reader, an optical reader, a magnetic reader, and a bar code reader.

23. A system to facilitate the automatic distribution of acquired images within a medical facility, said system comprising:
    means for displaying digital images within a first operatory of a medical facility;
    means for displaying digital images within a second operatory of a medical facility;
    means for scanning a scannable image medium to read an encoded identifier and a captured image from said scannable image medium, wherein said encoded identifier is associated with said first operatory or said second operatory; and
    means for transmitting said read image to said means for displaying digital images within said first operatory or to said means for displaying digital images within said second operatory in dependence on said read associated identifier.

24. The system of claim 23 further comprising:
    means for capturing an image on said scannable image medium within said first operatory; and
    means for capturing an image on said scannable image medium within said second operatory.

25. The system of claim 24 wherein said scannable image medium includes one of a radiographic film, a photographic film, and a photostimulable phosphor plate.

* * * * *